United States Patent [19]

Mercer et al.

[11] 4,085,101
[45] Apr. 18, 1978

[54] 1,3-DIARYL-2-PYRAZOLINE DERIVATIVES

[75] Inventors: Alec Victor Mercer, Leeds; Peter Stuart Littlewood, Ilkley; Ivan Joseph Bolton, Bingley, all of England; Fritz Fleck, Bottmingen, Switzerland

[73] Assignee: Sandoz Ltd., Basel, Switzerland

[21] Appl. No.: 683,409

[22] Filed: May 5, 1976

Related U.S. Application Data

[63] Continuation of Ser. No. 487,844, Jul. 11, 1974, abandoned.

[30] Foreign Application Priority Data

Jul. 18, 1973 United Kingdom ............... 34111/73

[51] Int. Cl.$^2$ ................. C07D 231/42; C07D 231/06; C07D 235/00; C07D 233/00
[52] U.S. Cl. .................................. 260/239.9; 548/379
[58] Field of Search .................. 260/239.6, 310, 239.7, 260/239.8, 239.9; 548/379

[56] References Cited

U.S. PATENT DOCUMENTS

| | | | |
|---|---|---|---|
| 3,378,389 | 4/1968 | Schellhammer et al. | 117/33.5 |
| 3,522,242 | 7/1970 | Schinzel et al. | 260/239.9 |
| 3,560,485 | 2/1971 | Schinzel et al. | 260/239.9 |
| 3,629,241 | 12/1971 | Krause et al. | 260/239.9 |
| 3,690,947 | 9/1972 | Roach et al. | 117/33.5 |
| 3,849,406 | 11/1974 | Aebli et al. | 260/239.9 |
| 4,003,889 | 1/1977 | Bolton et al. | 260/239.9 |

FOREIGN PATENT DOCUMENTS

| | | |
|---|---|---|
| 1,445,705 | 1/1969 | Germany. |
| 1,204,953 | 9/1970 | United Kingdom. |

*Primary Examiner*—Albert T. Meyers
*Assistant Examiner*—D. W. Robinson
*Attorney, Agent, or Firm*—Gerald D. Sharkin; Richard E. Vila; Joseph J. Borovian

[57] ABSTRACT

Disclosed are compounds of formula I,

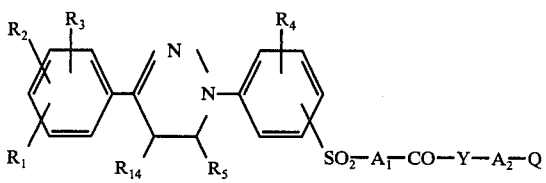

in which either $R_1$, $R_2$ and $R_3$, which may be the same or different, each signifies a hydrogen atom, a chlorine or fluorine atom, an alkyl radical of 1 to 4 carbon atoms, an alkoxy radical of 1 to 4 carbon atoms, a cyano group, a group —$SO_3M$, an unsubstituted phenyl radical or a phenyl radical substituted by up to 2 substituents selected from chlorine, fluorine, alkyl of 1 to 4 carbon atoms, alkoxy of 1 to 4 carbon atoms and the group —$SO_3M$, with the proviso that only one of $R_1$, $R_2$ and $R_3$ signifies an unsubstituted or substituted phenyl radical or two of $R_1$, $R_2$ and $R_3$, together, form a methylenedioxy group, the other of $R_1$, $R_2$ and $R_3$ having one of the above significances, $R_4$ signifies a hydrogen atom, a chlorine or fluorine atom, an alkyl radical of 1 to 4 carbon atoms or an alkoxy radical of 1 to 4 carbon atoms, $R_5$ signifies a hydrogen atom, an alkyl radical of 1 to 4 carbon atoms, an unsubstituted phenyl radical or a phenyl radical substituted by 1 or 2 substituents selected from chlorine, fluorine, alkyl of 1 to 4 carbon atoms, alkoxy of 1 to 4 carbon atoms and the group —$SO_3M$, $R_{14}$ signifies an alkyl radical of 1 to 8 carbon atoms, $A_1$ signifies a $C_1$ to $C_3$ alkylene chain, unsubstituted or substituted by up to two alkyl groups of 1 to 4 carbon atoms, Y signifies —O— or —$NR_6$—, in which $R_6$ signifies a hydrogen atom or an alkyl radical of 1 to 4 carbon atoms, Q signifies

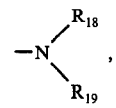

in which either $R_{18}$ and $R_{19}$, which may be the same or different, each signifies a hydrogen atom or an alkyl radical of 1 to 4 carbon atoms, or one of $R_{18}$ or $R_{19}$, together with $R_6$, signifies an ethylene bridge, the other signifying a hydrogen atom or alkyl radical of 1 to 4 carbon atoms, or Q signifies —$SO_3M$, or Q signifies —$SR_{21}$ or —$SR_{22}^\oplus R_{23}$ $An^\ominus$, in which $R_{21}$ signifies an alkyl radical of 1 to 4 carbon atoms, unsubstituted or substituted by a hydroxy radical or an alkoxy radical of 1 to 4 carbon atoms; or a phenyl or cycloalkyl radical of 5 to 7 carbon atoms, each unsubstituted or substituted by up to 2 substituents selected from chlorine, fluorine, $C_{1-4}$ alkyl and $C_{1-4}$ alkoxy, $R_{22}$ and $R_{23}$, which may be the same or different, each have a significance of $R_{21}$, above, with the proviso that both do not simultaneously signify unsubstituted or substituted phenyl or cycloalkyl radicals, $A_2$ signifies a $C_1$ to $C_3$ alkylene chain, unsubstituted or substituted by up to two alkyl groups of 1 to 4 carbon atoms; or a phenylene group, unsubstituted or substituted by up to 2 substituents selected from chlorine, fluorine, alkyl of 1 to 4 carbon atoms, alkoxy of 1 to 4 carbon atoms and the group —$SO_3M$, $An^\oplus$ signifies a colorless organic or inorganic anion, and the M's, which may be the same or different, each signifies a hydrogen atom, or a non-chromophoric cation, which compounds, where Q signifies

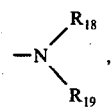
may be in quaternary ammonium salt form or in acid addition salt form, their production and use as optical brightening agents.
13 Claims, No Drawings

1,3-DIARYL-2-PYRAZOLINE DERIVATIVES

This is a continuation of application Ser. No. 487,844 filed July 11, 1974, now abandoned.

The invention relates to pyrazoline compounds.

The invention provides compounds of formula I,

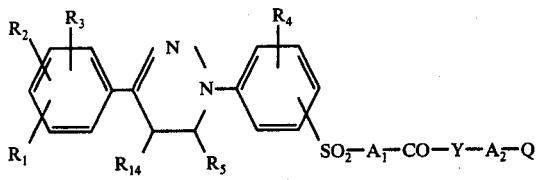

in which either $R_1$, $R_2$ and $R_3$, which may be the same or different, each signifies a hydrogen atom, a chlorine or fluorine atom, an alkyl radical of 1 to 4 carbon atoms, an alkoxy radical of 1 to 4 carbon atoms, a cyano group, a group —$SO_3M$, an unsubstituted phenyl radical or a phenyl radical substituted by up to 2 substituents selected from chlorine, fluorine, alkyl of 1 to 4 carbon atoms, alkoxy of 1 to 4 carbon atoms and the group —$SO_3M$, with the proviso that only one of $R_1$, $R_2$ and $R_3$ signifies an unsubstituted or substituted phenyl radical, or two of $R_1$, $R_2$ and $R_3$, together, form a methylenedioxy group, the other of $R_1$, $R_2$ and $R_3$ having one of the above significances, $R_4$ signifies a hydrogen atom, a chlorine or fluorine atom, an alkyl radical of 1 to 4 carbon atoms or an alkoxy radical of 1 to 4 carbon atoms, $R_5$ signifies a hydrogen atom, an alkyl radical of 1 to 4 carbon atoms, an unsubstituted phenyl radical or a phenyl radical substituted by 1 or 2 substituents selected from chlorine, fluorine, alkyl of 1 to 4 carbon atoms, alkoxy of 1 to 4 carbon atoms and the group —$SO_3M$, $R_{14}$ signifies an alkyl radical of 1 to 8 carbon atoms, $A_1$ signifies a $C_1$ to $C_3$ alkylene chain, unsubstituted or substituted by up to two alkyl groups of 1 to 4 carbon atoms, Y signifies —O— or —$NR_6$—, in which $R_6$ signifies a hydrogen atom or an alkyl radical of 1 to 4 carbon atoms, Q signifies

in which either $R_{18}$ and $R_{19}$, which may be the same or different, each signifies a hydrogen atom or an alkyl radical of 1 to 4 carbon atoms, or one of $R_{18}$ or $R_{19}$, together with $R_6$, signifies an ethylene bridge, the other signifying a hydrogen atom or alkyl radical of 1 to 4 carbon atoms, or Q signifies —$SO_3M$, or Q signifies —$SR_{21}$ or —$S^{\oplus}R_{22}R_{23}An^{\ominus}$, in which $R_{21}$ signifies an alkyl radical of 1 to 4 carbon atoms, unsubstituted or substituted by a hydroxy radical or an alkoxy radical of 1 to 4 carbon atoms; or a phenyl or cycloalkyl radical of 5 to 7 carbon atoms, each unsubstituted or substituted by up to 2 substituents selected from chlorine, fluorine, $C_{1-4}$ alkyl and $C_{1-4}$ alkoxy, $R_{22}$ and $R_{23}$, which may be the same or different, each have a significance of $R_{21}$, above, with the proviso that both do not simultaneously signify unsubstituted or substituted phenyl or cycloalkyl radicals, $A_2$ signifies a $C_1$ to $C_3$ alkylene chain, unsubstituted or substituted by up to two alkyl groups of 1 to 4 carbon atoms; or a phenylene group, unsubstituted or substituted by up to 2 substituents selected from chlorine, fluorine, alkyl of 1 to 4 carbon atoms, alkoxy of 1 to 4 carbon atoms and the group —$SO_3M$, $An^{\ominus}$ signifies a colourless organic or inorganic anion, and the M's, which may be the same or different, each signifies a hydrogen atom, or a non-chromophoric cation, which compounds, where Q signifies

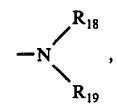

may be in quaternary ammonium salt form or in acid addition salt form.

The invention also provides a process for the production of compounds of formula I, characterised by
(a) reacting a compound of formula II,

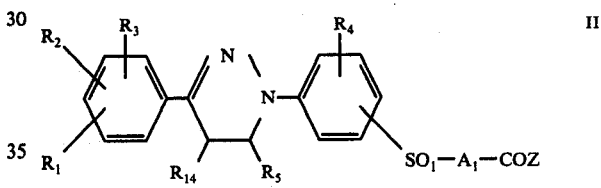

in which $R_1$, $R_2$, $R_3$, $R_4$, $R_5$, $R_{14}$ and $A_1$ are as defined above, and Z signifies a halogen atom, a hydroxy group or an alkoxy radical of 1 to 2 carbon atoms, with a compound of formula III,

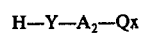

H—Y—$A_2$—Qx    III in which Y and $A_2$ are as defined above, and Qx has the same significance as Q, above, with the proviso that it signifies other than —$S^{\oplus}R_{22}R_{23}An^{\ominus}$, (b) reacting a compound of formula IV,

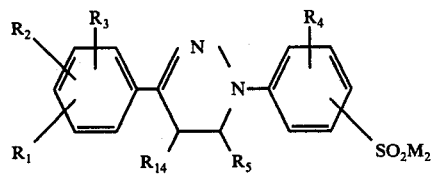

in which $R_1$, $R_2$, $R_3$, $R_4$, $R_5$ and $R_{14}$ are as defined above, and $M_2$ signifies a hydrogen atom or an alkali metal cation, with a compound of formula V,

$Z_1$—$A_1$—CO—Y—$A_2$—Qx    V in which $A_1$, $A_2$, Y and Qx are as defined above, and Z signifies a halogen atom,
(c) obtaining a compound of formula Ia,

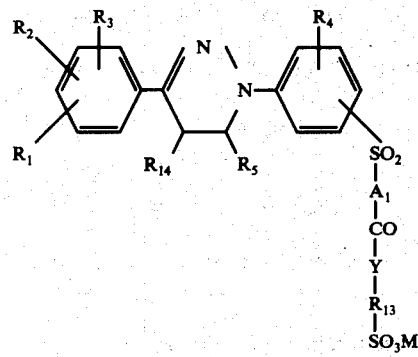

in which $R_1$, $R_2$, $R_3$, $R_4$, $R_5$, $R_{14}$, $A_1$, Y and $M_2$ are as defined above, and
$R_{13}$ signifies a $C_3$ alkylene chain, unsubstituted or substituted by up to two alkyl radicals of 1 to 4 carbon atoms,
by reacting a compound of formula IX,

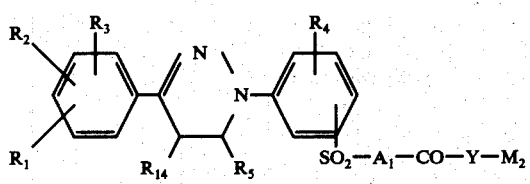

in which $R_1$, $R_2$, $R_3$, $R_4$, $R_5$, $R_{14}$, $A_1$, Y and $M_2$ are as defined above,
with a compound of formula X,

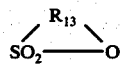

in which $R_{13}$ is as defined above,
(d) obtaining a compound of formula Ib,

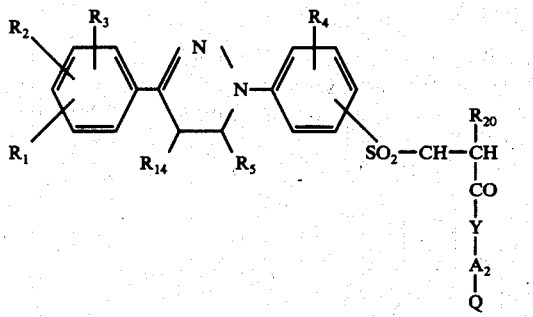

in which $R_1$, $R_2$, $R_3$, $R_4$, $R_5$, Y, $A_2$ and Q are as defined above, and
$R_{20}$ signifies a hydrogen atom or an alkyl radical of 1 to 4 carbon atoms,
by reacting a compound of formula IV, stated above, with a compound of formula XI,

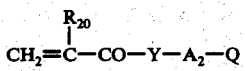

in which $R_{20}$, Y, $A_2$ and Q are as defined above, and where, in the resulting product Q signifies $-SR_{21}$ and a compound wherein Q signifies $-S^{\oplus}R_{22}R_{23}An^{\ominus}$ is desired, converting said $-SR_{21}$ group into a $-SR_{22}R_{23}An^{\ominus}$, and where, in the resulting product Q signifies $-NR_{18}R_{19}$ and a compound in quaternary ammonium or acid addition salt form is required, quaternating or protonising such group.

The above processes may be carried out in manner conventional for the types of reaction involved.

Process (a) is suitably carried out in the absence of a solvent, in water, in a non-polar solvent, such as chlorobenzene, xylene or trichloroethylene, in a polar organic solvent, or in an aqueous organic solvent, such as in aqueous acetone, aqueous dimethylformamide or aqueous dioxan. A suitable reaction temperature is from 0° to 200° C, preferably from 10° to 150° C. Where, in the compound of formula II, Z signifies a halogen atom, the reaction is suitably carried out in the presence of a base acceptor, such as sodium carbonate or sodium hydroxide and, where Z signifies a hydroxy or alkoxy radical, in the presence of an acid catalyst such as sulphuric acid, hydrogen chloride or p-toluenesulphonic acid. In the compound of formula III, Q is preferably other than $-NH_2$.

Process (b) may suitably be carried out in water, a polar organic solvent or in an aqueous organic solvent medium, such as in aqueous ethanol or isopropanol, aqueous acetone, aqueous dioxan or aqueous dimethylformamide. A suitable reaction temperature is from 20° to 150° C, preferably from 50° to 120° C. The reaction is suitably carried out at a pH of from 3 to 10, preferably from 5 to 8.

Process c) is conveniently carried out in an inert organic solvent such as in acetone, dimethylformamide or dioxan. A suitable reaction temperature is from 20° to 200° C, preferably from 50° to 150° C.

Process (d) is conveniently carried out in water, a polar organic solvent or in an aqueous organic solvent, such as in aqueous ethanol, isopropanol, acetone, dioxan or dimethylformamide. A suitable reaction temperature is from 20° to 150° C, preferably from 50° to 150° C. The reaction may conveniently be carried out under from mildly acidic to mildly basic conditions, e.g. from pH 3 to 9, preferably from 4 to 8. In the compound of formula XI, Q is preferably other than $-S^{\oplus}R_{22}R_{23}An^{\ominus}$.

The conversion of any group $-SR_{21}$ into a group $-S^{\oplus}R_{22}R_{23}An^{\ominus}$ may be carried out in conventional manner, as may quaternisation or protonation of any group $-NR_{18}R_{19}$.

The compounds of formulae II, III, IV, V, IX, X and XI are either known or may be obtained in conventional manner from available starting materials.

The resulting compounds of formula I may be isolated and purified in conventional manner. As will be appreciated, conversion of compounds of formula I, bearing one or more $-SO_3M$ groups, in free acid form, to salt forms and vice versa may be carried out, as desired, in conventional manner, as can interconversion of salt forms, e.g. from sodium to ammonium salt forms. As indicated above, where the compounds of formula I contain a plurality of $-SO_3M$ groups, the M's may be the same or different. Thus, partial and mixed salt forms of the compounds are embraced by the invention.

As examples of suitable acid addition salt forms of the compound of formula I, in which Q signifies $-NR_{18}R_{19}$, may be given mineral acid salt forms such as the hydrochloride, sulphate and phosphate, and organic acid salt forms such as the formate, oxalate, maleate, acetate and propionate.

As examples of suitable quaternary salt forms of compounds of formula I, wherein Q signifies —NR$_{18}$R$_{19}$, may be given such forms produced by quaternising by reaction with alkylating agents such as alkyl halides and dialkyl sulphates, in which the alkyl radicals are preferably of 1 to 4 carbon atoms.

As examples of suitable anions, An$^\ominus$, present in the compounds of formula I, in which Q signifies —S$^\oplus$R$_{22}$R$_{23}$An$^\ominus$, may be given inorganic ions such as chloride, sulphate and phosphate ions, organic ions such as formate, oxalate, maleate, acetate and propionate, and alkyl sulphate ions of 1 to 4 carbon atoms such as methosulphate and ethosulphate ions. Where, in the compounds of formula I, two of R$_1$, R$_2$ and R$_3$, together, signify a methylenedioxy radical, the other of R$_1$, R$_2$ and R$_3$ is preferably other than phenyl. Indeed, where a methylenedioxy group is borne by the 3-phenyl group, such is preferably the sole substituent. Any alkyl substituent on an alkylene radical as A$_1$ or A$_2$ is preferably of one or two carbon atoms, more preferably of one carbon atom. Preferably no more than one of R$_1$, R$_2$ and R$_3$ signifies a substituent selected from —SO$_3$M or —CN.

Preferred compounds of formula I are the compounds of formula I',

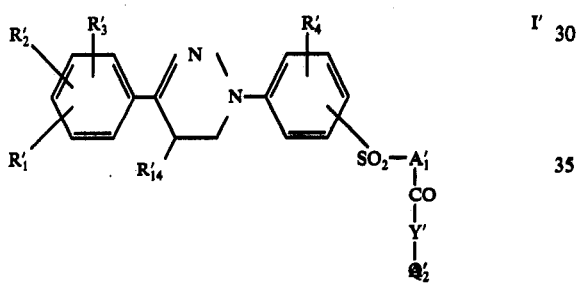

in which R$_1'$, R$_2'$ and R$_3'$, independently, signify hydrogen, chlorine, fluorine, C$_{1-4}$alkyl or C$_{1-4}$alkoxy,
R$_4'$ signifies hydrogen, chlorine, fluorine, C$_{1-4}$alkyl or C$_{1-4}$ alkoxy,
R$_{14}'$ signifies C$_{1-4}$alkyl,
A$_1'$ signifies unsubstituted C$_1$-C$_3$ alkylene,
Y' signifies —O— or

in which R$_6'$ signifies hydrogen or C$_{1-2}$ alkyl,
Q' signifies

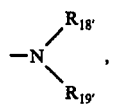

in which R$_{18}'$ and R$_{19}'$, independently, signify C$_{1-4}$alkyl
or Q' signifies —SO$_3$M, where M is as defined above,
or Q' signifies —SR$_{21}'$ or —S$^\oplus$R$_{21}'$R$_{22}'$An$^\ominus$, where R$_{21}'$ and R$_{22}'$, independently, signify C$_{1-4}$alkyl,
A$_2'$ signifies unsubstituted C$_1$-C$_3$ alkylene or unsubstituted phenylene, and
An$^\ominus$ is as defined above, which compounds, where Q' signifies —NR$_{18}'$R$_{19}'$ may be in quaternary ammonium or acid addition salt form.

Representative of the compounds of formula I' may be given the compounds of formulae Ia' and Ib',

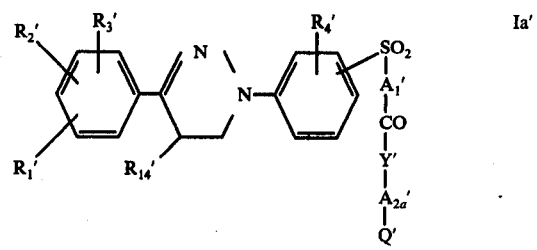

in which R$_1'$, R$_2'$, R$_3'$, R$_4'$, R$_{14}'$, A$_1'$, Y' and Q' are as defined above, and
A$_{2a}'$ signifies an unsubstituted C$_1$-C$_3$ alkylene chain,

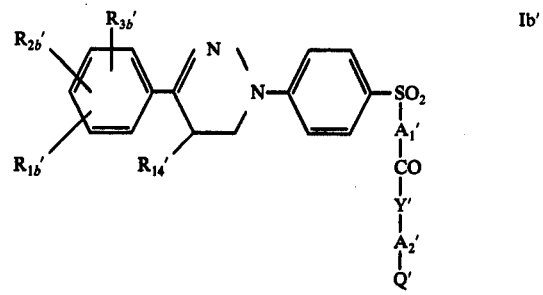

in which R$_{14}'$, A$_1'$, A$_2'$, Y$_1'$ and Q' are as defined above, and
R$_{1b}'$, R$_{2b}'$ and R$_{3b}'$, independently, signify hydrogen, chlorine or C$_{1-4}$alkyl,
which compounds of formula Ia' and Ib', where Q signifies NR$_{18}'$R$_{19}'$ may be in quaternary ammonium or acid addition salt form.

In the compounds of formulae I', Ia' and Ib', preferred anions as An$^\ominus$, when Q signifies —SR$_{21}'$R$_{22}'$An$^{63}$, are the ethosulphate and methosulphate anions.

As examples of alkyl and alkoxy radicals may be given methyl, ethyl, n-propyl, isopropyl and butyl, and methoxy, ethoxy, n-propyloxy, iso-propyloxy and butoxy.

Preferred compounds of formula I' are the compounds of formula I'',

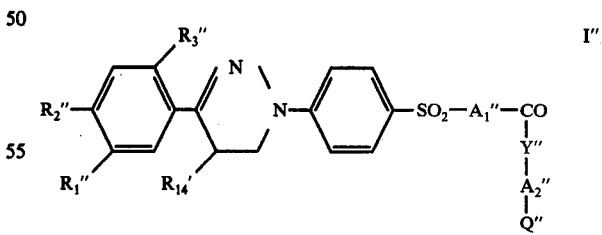

in which R$_1''$, R$_2''$ and R$_3''$, independently, signify hydrogen, chlorine or C$_{1-2}$alkyl,
A$_1''$ signifies unsubstituted C$_{1-2}$-alkylene,
Y'' signifies —O—, —NH— or —NCH$_3$—, and
Q'' signifies —NR$_{18}'$R$_{19}'$, where R$_{18}'$ and R$_{19}'$ are as defined above,
or Q'' signifies —SO$_3$M, where M is as defined above,
A$_2''$ signifies unsubstituted C$_{2-3}$-alkylene or unsubstituted phenylene, and $R_{14}'$ is as defined above, which compounds, where Q″ signifies —NR$_{18}$'R$_{19}$' may be in quaternary ammonium or acid addition salt form.

Representative of the compounds of formula I″ may be given the compounds of formulae Ia″ and Ib″,

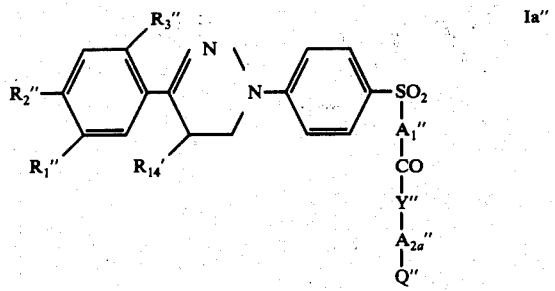

in which $R_1''$, $R_2''$, $R_3''$, $R_{14}'$, $A_1''$ and Q″ are as defined above, and $A_{2a}''$ signifies unsubstituted $C_{2-3}$-alkylene,

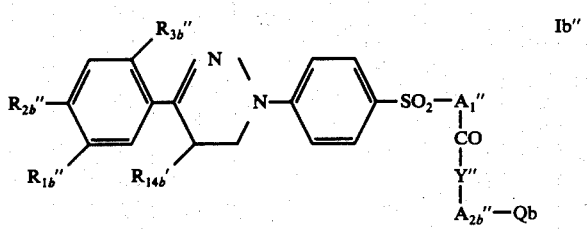

in which $A_1''$ and Y″ are as defined above, $R_{1b}''$, $R_{2b}''$ and $R_{3b}''$, independently, signify hydrogen, chlorine or methyl, $R_{14b}'$ signifies $C_{1-2}$alkyl, Qb″ signifies —NR$_{18}$″R$_{19}$″, where $R_{18}''$ and $R_{19}''$, independently, signify $C_{1-2}$alkyl, or Qb″ signifies —SO$_3$M, where M is as defined above, and $A_{2b}''$ signifies unsubstituted ethylene or phenylene, which compounds of formulae Ia″ and Ib″, where Q signifies dialkylamino, may be in quaternary ammonium or acid addition salt form.

In the compounds of formulae I, Ia′, Ib′, I″, Ia″ and Ib″, where Q signifies —SO$_3$M, and M signifies a cation, the exact nature thereof is not critical provided it is not chromophoric. It may thus be any conventional anion employed in the optical brightener art, to which the present invention relates. As examples of preferred cations may be given the alkali-metal cations, such as of sodium, potassium and lithium, the ammonium cation and alkyl- and alkanolammonium cations, e.g. of formula R$_7$R$_8$R$_9$N$^\oplus$H, where R$_7$, R$_8$ and R$_9$, independently, signify hydrogen or $C_{1-4}$alkyl, unsubstituted or substituted by up to two substituents selected from $C_{1-2}$alkyl and hydroxy, e.g. mono-, di- and tri-ethanolammonium and mono-, di- and tri-isopropanolammonium cations. The preferred cations are the alkalimetal, particularly sodium, cations and the ammonium cation, the most preferred being the sodium cation. Divalent, e.g. alkaline earth metal, cations, and polyvalent, e.g. aluminium cations, are also possible. However, for the sake of simplicity, in the formulae herein, M has been shown as mono-valent.

In the compounds of the invention, A$_2$ should be phenylene only when Q signifies —SO$_3$M.

The preferred compounds of the invention are those in which Q signifies —SO$_3$M.

The compounds of formula I are useful as optical brightening agents.

The compounds of formula I, particularly those in which Q signifies —SO$_3$M or —NR$_{18}$R$_{19}$, give good results as optical brightening agents on natural or synthetic polyamide fibres, particularly on Nylon 6, Nylon 6.6 and wool fibres. Thus, the invention also provides a process for optically brightening natural or synthetic polyamide fibres, particularly Nylon 6, Nylon 6.6 and wool fibres, comprising applying thereto, as optical brigthening agent, a compound of formula I.

The compounds of formula I may be applied to the polyamide fibres, which may, for example, be in yarn, non-woven, woven or knitted form, in conventional manner, for example by the so-called "THERMOSOL" application method, (Gunn and Nightingale "Cotton and Man-Made Fibres Year Book" 1966–67 p. 410).

In such process the compounds are applied in an amount of from 0.01% to 0.7%, preferably 0.05% to 0.3% based on the weight of substrate. The substrate is padded with liquor at a temperature of from 0° to 60° C, preferably 10° to 50° C at a pick-up of from 20 to 120%, preferably 40 to 90%, the liquor containing such additives as surfactants and formic acid etc. as desired. The subsequent heat treatment is applied for 5 to 120 secs., preferably 15 to 60 secs., the temperature being 140° C to 190° C, preferably 160° to 185° C, for Nylon 6, and 140° to 220° C, preferably 170° to 200° C for Nylon 6.6.

The compounds give notably bright effects when applied by this method and the brightened pieces show notably good light fastness. Other methods include the so-called "acid-flash" procedure and exhaust, acid or neutral bath, methods.

Further, the compounds of formula I, in which Q signifies —NR$_{18}$R$_{19}$, —SR$_{21}$ or —S$^\oplus$R$_{22}$R$_{23}$ An$^\ominus$, give good brightening effects when applied to fibres of polyacrylonitrile and its co-polymers.

The compounds may be applied to the fibres, in, for example, yarn, non-woven, woven or knitted form, in conventional manner, for example using exhaust bath techniques. For example, a polyacrilonitrile substrate may be introduced into a bath, at 40° C, containing from 0.01% to 1.0%, preferably 0.05% to 0.5% of brightener, and 1.0% to 5.0%, preferably 2.0% to 4.0% of acetic acid, based on the weight of the substrate. A suitable liquor to goods ratio is from 5:1 to 100:1, preferably from 15:1 to 50:1. The bath is then heated to 90° to 95° C, during 15 to 60, preferably 20 to 40, minutes and maintained at this temperature for 15 to 120, preferably 30 to 60, minutes. The substrate is then removed and rinsed, preferably first with warm water and then cold water, and then dried.

The compounds of formula I, in which Q signifies —SR$_{21}$ are further indicated for use as optical brightening agents for substrates comprising or consisting of cellulose diacetate or cellulose triacetate fibres, to which substrates such compounds may be applied in conventional manner and in conventional amounts.

The invention is further illustrated in the following Examples in which parts and percentages are by weight and temperatures in degrees centigrade.

EXAMPLE 1

4-chloro-α-chloromethyl propiophenone (21.7 g) and 4-β-carboxyethylsulphonyl phenylhydrazine hydrochloride (28.1 g) were slurried together in isopropanol (100 ml) and water (50 ml). The pH of the slurry was adjusted to 2–3 with 30% sodium hydroxide solution and the mixture was then heated to the boil. The pH was maintained at 2–3 by the addition of 30% sodium hydroxide solution whilst the mixture was stirred and boiled for two hours. The mixture was then cooled to 10°, filtered, and the filter cake washed with water (100 ml) and dried to give 1-(β-carboxyethylsulphonylphenyl)-3-p-chlorophenyl-4-methyl-Δ²-pyrazoline as a pale yellow solid.

The pyrazoline acid thus obtained was slurried in trichloroethylene (200 ml) and the mixture heated to the boil. Dimethylformamide (0.2 ml) was added, followed by thionyl chloride (12.0 g) over a period of 15 minutes. The mixture was stirred under reflux for two hours, cooled to 10°–15°, filtered, and the filter cake washed with cold trichloroethylene (20 ml).

The crude acid chloride thus obtained was dissolved in acetone (120 ml) and added over a period of 5 minutes to a well stirred solution of N-methyl taurine sodium salt (12.9 g) in water (60 ml). The pH of the reaction mixture was maintained at 6.5 to 7.5 by the addition of sodium bicarbonate, and stirring was continued for one hour at ambient temperature. The mixture was heated to reflux, sodium chloride (20 g) was added, and the resulting solution cooled to give the pyrazoline The 4-chloro-α-chloromethyl propiophenone was obtained as follows:

A steady stream of dry hydrogen chloride was bubbled through a solution of methacrylonitrile (12.3 g) in ether (25 ml) for eight hours. The solution was evaporated to dryness, and the residue heated under reflux for four hours with hydrochloric acid (20 ml, d 1.14) and water (20 ml). The mixture was diluted with water (80 ml) and extracted with benzene (2 × 100 ml). The combined benzene extracts were dried over sodium sulphate and evaporated to dryness. The residue was mixed with thionyl chloride (18 ml), 10 drops of dimethylformamide were added, and the mixture was heated at 60° for 2 hours. The resultant mixture was evaporated to dryness, and the residue distilled to give 17.6 g of 2-methyl-3-chloropropionyl chloride, b.p. 30°–40° /5–10 mm. This acid chloride (17.6 g) was added over 15 minutes to a mixture of chlorobenzene (13.2 ml) and anhydrous aluminium chloride (17.6 g) was added over 15 minutes to a mixture of chlorobenzene (13.2 ml) and anhydrous aluminium chloride (17.6 g) maintained at 45°–50°. The mixture was maintained at 50° for one hour, and was then poured onto ice (50 g), water (100 ml) and hydrochloric acid (20 ml, d 1.14) to give 21.7 g of 4-chloro-α-chloromethyl propiophenone.

By repeating the procedure of Example 1, but using

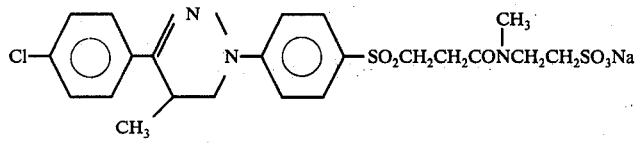

as a pale yellow solid.

appropriate starting materials, the compounds shown in the following table may be obtained.

| Example | Compound | Appearance |
|---|---|---|
| 1a | Cl–[ring]–C(=N–N–[ring]–SO₂CH₂CH₂CONHCH₂CH₂SO₃Na)–CH(CH₃)– | pale yellow solid |
| 1b | Cl–[ring]–C(=N–N–[ring]–SO₂CH₂CH₂CONH–[ring]–SO₃Na)–CH(CH₃)– | pale yellow solid |
| 1c | Cl–[ring]–C(=N–N–[ring]–SO₂CH₂CH₂CONH–[ring]–SO₃Na)–CH(CH₃)– | pale yellow solid |
| 1d | Cl–[ring]–C(=N–N–[ring]–SO₂CH₂CH₂CON(CH₃)CH₂CH₂SO₃Na)–CH(C₂H₅)– | pale yellow solid |
| 1e | [ring]–C(=N–N–[ring]–SO₂CH₂CH₂CON(CH₃)CH₂CH₂SO₃Na)–CH(CH₃)– | off white solid |

| Example | Compound | Appearance |
|---|---|---|
| 1f | [structure: 3,4-dichlorophenyl pyrazoline with —SO₂CH₂CH₂CON(CH₃)CH₂CH₂SO₃Na substituent] | yellow solid |
| 1g | [structure: 4-fluorophenyl pyrazoline with —SO₂CH₂CH₂CONH—phenyl—SO₃Na] | off white solid |
| 1h | [structure: 4-methoxyphenyl pyrazoline with —SO₂CH₂CH₂CONH—phenyl—SO₃Na] | pale yellow solid |

EXAMPLE 2

The crude pyrazoline acid chloride prepared from 21.7 g 4-chloro-α-chloromethyl propiophenone according to Example 1 was slurried in trichloroethylene (100 ml) at 25°. Dimethylaminopropylamine (10.2 g) was added dropwise to the stirred slurry over 10 minutes, and the resulting mixture was stirred for a further hour at 25°. Sodium hydroxide (3.2 g) and water (2 ml) were added to the reaction mixture, which was heated to the boil and then allowed to cool to ambient temperature to give the pyrazoline.

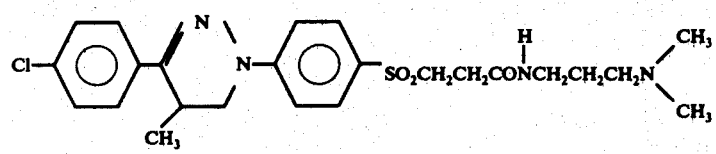

as an off white solid.

By repeating the procedures of Example 2, but using appropriate starting materials, the compounds shown in the following table can be obtained.

| Example | Compound | Appearance |
|---|---|---|
| 2a | [structure: 3,4-dichlorophenyl pyrazoline with —SO₂CH₂CH₂CONHCH₂CH₂CH₂N(CH₃)₂] | yellow solid |
| 2b | [structure: 3,4-dichlorophenyl pyrazoline with —SO₂CH₂CH₂CONHCH₂CH₂N(CH₃)₂] | yellow solid |
| 2c | [structure: 3,4-dichloro-with methyl pyrazoline with —SO₂CH₂CH₂CONHCH₂CH₂CH₂N(CH₃)₂] | pale yellow solid |
| 2d | [structure: phenyl pyrazoline with —SO₂CH₂CH₂CONHCH₂CH₂N(CH₃)₂] | off white solid |

EXAMPLE 3

The crude pyrazoline acid chloride prepared from 21.7 g 4-chloro-α-chloromethyl propiophenone according to Example 1 was slurried in β-methylthioethanol (50 ml). The mixture was warmed to 60° and stirred at 50° – 60° for one hour. The mixture was then cooled to ambient temperature and treated with ethanol (100 ml) to give the pyrazoline

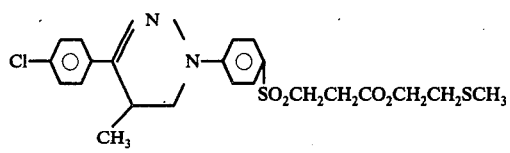

The crude pyrazoline ester was slurried in dioxan (400 ml). Dimethyl sulphate (20 g) was added and the mixture was heated under reflux for one hour and then cooled. A pyrazoline of formula

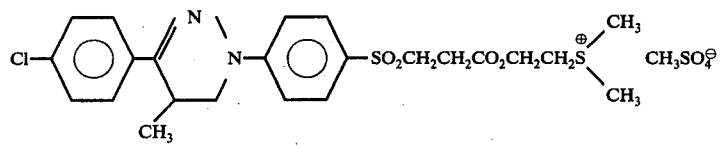

precipitated as a pale yellow water soluble oil.

EXAMPLE 4

1-(β-carboxyethylsulphonyl phenyl)-3-(p-chlorophenyl)-4-methyl-Δ²-pyrazoline sodium salt (42.85 g) was slurried in a mixture of dioxan (500 ml) and propane sultone (15.0 g). The mixture was heated under reflux for 16 hours, cooled, filtered, and washed with acetone to give a pyrazoline of formula

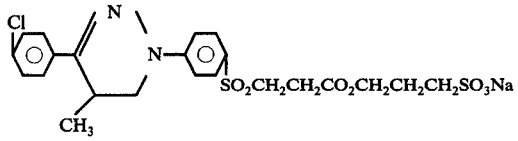

as a pale yellow solid.

EXAMPLE 5

Chloroacetyl chloride (17.0 g) was added over fifteen minutes to a stirred solution of N-methyl taurine sodium salt (24.15 g) in water (45 ml) at 0°–5°. The pH of the reaction mixture was maintained at 7–8 by the addition of anhydrous sodium carbonate, and the temperature of the mixture was allowed to rise to 20° over 1 hour. 3-(p-chlorophenyl)-4-methyl-Δ²-pyrazoline-1-(p-phenylsulphinic acid) sodium salt (35.65 g), water (100 ml) and dimethylformamide (200 ml) were added and the resultant mixture was heated under reflux for 16 hours. Sodium chloride (20 g) was added and the mixture cooled to give the pyrazoline

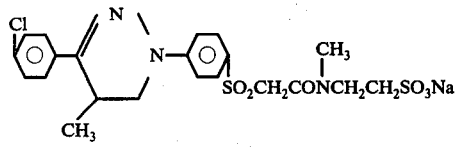

as a pale yellow solid.

EXAMPLE 6

β-chloropropionyl chloride (19.1 g) was added over a period of 15 minutes to a well stirred solution of N-methyl taurine sodium salt in water (45 ml) at 0°–5°. The pH of the reaction mixture was maintained at 7–8 by the addition of sodium carbonate, and the temperature of the mixture was allowed to rise to 20° over one hour. Sodium hydroxide (6.0 g) in water (15 ml) was added dropwise at 20°–30°. 3-(3',4'-dichloro-6'-methyl)-phenyl-4-methyl-Δ²-pyrazoline-1-(p-phenylsulphinic acid) sodium salt (40.5 g), water (100 ml) and 2-ethoxyethanol (200 ml) were then added and the pH of the resultant mixture was adjusted to 4 with glacial acetic acid. The mixture was heated under reflux for 6 hours, sodium chloride (20 g) was added and the mixture cooled to give the pyrazoline

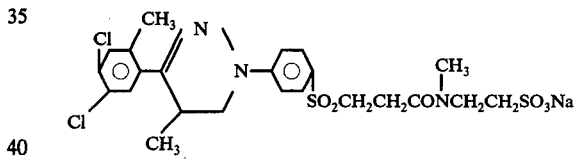

as a pale yellow solid.

The 3-(3',4'-dichloro-6'-methyl)-phenyl-4-methyl-Δ²-pyrazoline-1-(p-phenylsulphinic acid) sodium salt was obtained as follows:

2-methyl-4,5-dichloro-α-chloromethyl propiophenone (53.0 g), p-hydrazinobenzene sulphonic acid (41.4 g), and sodium acetate (49.2 g) were slurried in dimethylformamide (400 ml) and water (80 ml). The mixture was heated to the boil and stirred under reflux for 16 hours. Water (320 ml) and sodium chloride (40 g) were added, and the hot mixture allowed to cool. The resultant yellow solid was filtered, washed with 10% brine and dried.

The crude product was slurried in dimethylformamide (180 ml) and thionyl chloride (24.0 ml) was added dropwise over 10 minutes. The mixture was heated to 50° for 1 hour, cooled, filtered and the filter cake washed with ice cold water. The resultant yellow solid was slurried in 2-ethoxyethanol (210 ml) and a solution of sodium sulphide dihydrate (42.6 g) in water (150 ml) was added over 10 minutes. The mixture was heated to 40° for one hour, cooled and filtered to give 40.5 g of 3-(3',4'-dichloro-6'-methyl)-phenyl-4-methyl-Δ²-pyrazoline-1-(p-phenylsulphinic acid) sodium salt.

By repeating the procedure of Example 6, but using appropriate starting materials, the compounds shown in the following table can be obtained.

| Example | Compound | Appearance |
|---|---|---|
| 7 | Cl—⟨Ar(CH₃,CH₃)⟩—C(=N-N-⟨Ar⟩-SO₂CH₂CH₂CONCH₂CH₂SO₃Na)(CH-CH₃)(CH₃) | off white solid |
| 8 | Cl—⟨Ar⟩—C(=N-N-⟨Ar(Cl)⟩-SO₂CH₂CH₂CONCH₂CH₂SO₃Na)(CH-CH₃)(CH₃) | pale yellow solid |
| 9 | Cl—⟨Ar⟩—C(=N-N-⟨Ar(OCH₃)⟩-SO₂CH₂CH₂CONCH₂CH₂SO₃Na)(CH-CH₃)(CH₃) | pale yellow solid |
| 10 | Cl—⟨Ar⟩—C(=N-N-⟨Ar(CH₃)⟩-SO₂CH₂CH₂CONCH₂CH₂SO₃Na)(CH-CH₃)(CH₃) | pale yellow solid |

APPLICATION EXAMPLE A

A 5 g piece of white Nylon 6.6 was treated with 200 ml of a solution containing 25 milligrams of the pyrazoline produced in Example 1 and 150 mg of acetic acid. The piece was entered at 40°, the temperature of the bath increased to 90°-100° over 30 minutes and then maintained at 90°-100° for a further 30 minutes. The piece was removed from the bath, rinsed in cold demineralised water and dried in an oven at 80°. The treated piece showed a brilliant whiteness compared to the untreated piece.

APPLICATION EXAMPLE B

A strip of white Nylon 6.6, 15 cc wide and weighing 8 g, was padded at 100% expression through a solution containing 0.2% of the pyrazoline produced in Example 1, 2% of a non-ionic alkylene oxide adduct of an alkylated phenol, and 0.2% formic acid. The nylon piece was dried at 80° C and then passed through an oven at 180° for 30 seconds. The treated piece showed a brilliant whiteness compared with the untreated piece.

APPLICATION EXAMPLE C

A strip of Nylon 6.6, 15 cm wide and weighing 8 g, was padded at 100% expression through a solution containing 0.2% of the pyrazoline produced in Example 1. The nylon piece was boiled for 1 minute in 240 ml of water containing 0.2% acetic acid, and was then washed off in boiling water for 1 minute. The piece was then rinsed in cold demineralised water and dried in an oven at 80°. The treated piece showed a brilliant whiteness compared to the untreated piece.

APPLICATION EXAMPLE D

A 5 g piece of white Orlon 75 polyacrylonitrile was entered at room temperature into 200 milliliters of an aqueous solution containing 15 milligrams of the pyrazoline produced in Example 2 and 15 milligrams of acetic acid. The pyrazoline was added to the liquor as a solution in 0.1% aqueous acetic acid. The temperature of the liquor was raised to 90° over 30 minutes, and maintained at 90°-100° for a further 60 minutes, after which the piece was removed from the dyebath, rinsed in hot, then cold demineralised water, and dried in an oven at 80°. The treatment imparted a brilliant whiteness to the fabric.

APPLICATION EXAMPLE E

The procedure of application Example B was repeated, but using 0.2% of the pyrazoline produced in Example 1c. The treated piece of nylon showed a brilliant whiteness compared with the untreated piece.

APPLICATION EXAMPLE F

The procedure of application Example C was repeated, but using 0.2% of the pyrazoline produced in Example 1c. The treated piece of nylon showed a brilliant whiteness compared with the untreated piece.

What is claimed is:

1. A compound of the formula i,

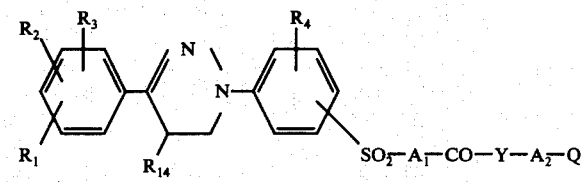

wherein $R_1$, $R_2$, $R_3$ and $R_4$, independently, are hydrogen, chloro, fluoro, $C_{1-4}$alkyl or $C_{1-4}$alkoxy, $R_{14}$ is $C_{1-4}$alkyl, $A_1$ is unsubstituted $C_{1-3}$alkylene, $A_2$ is unsubstituted $C_{1-3}$alkylene or phenylene, Y is —O— or

in which $R_6$ is hydrogen or $C_{1-2}$alkyl, and

Q is —$NR_{18}R_{19}$, where $R_{18}$ and $R_{19}$, independently, are $C_{1-4}$alkyl, or the quaternary ammonium or acid addition salts thereof.

2. A compound of claim 1, wherein $R_1$, $R_2$ and $R_3$, independently, are hydrogen, chloro or $C_{1-4}$alkyl.

3. A compound of claim 2, wherein $R_1$, $R_2$ and $R_3$, independently, are hydrogen, chloro or methyl.

4. A compound of claim 1, in which $R_4$ is hydrogen.

5. A compound of claim 1, wherein $R_4$ is hydrogen, chloro, $C_{1-4}$alkyl or $C_{1-4}$alkoxy and Y is —O—, —NH— or —NCH—.

6. A compound of claim 5, wherein $R_4$ signifies hydrogen and $R_{14}$ is methyl or ethyl.

7. A compound of claim 6, in which $R_1$, $R_2$ and $R_3$, independently, are hydrogen, chloro or $C_{1-4}$alkyl.

8. A compound of claim 7, wherein $R_1$, $R_2$ and $R_3$, independently, are hydrogen, chloro or methyl.

9. A compound of claim 8, wherein $R_{14}$ is methyl.

10. A compound of claim 5, wherein $A_1$ is unsubstituted $C_{1-2}$alkylene and $A_2$ signifies unsubstituted $C_{2-3}$alkylene.

11. A compound of claim 1, wherein $R_1$, $R_2$ and $R_3$, independently, are hydrogen, chloro or $C_{1-2}$alkyl, $R_4$ is hydrogen, $A_1$ is unsubstituted $C_{1-2}$alkylene, $A_2$ is unsubstituted $C_{2-3}$alkylene or unsubstituted phenylene and Y is —O—, —NH or —$NCH_3$.

12. A compound of claim 11, wherein $A_2$ unsubstituted $C_{2-3}$alkylene.

13. A compound of claim 11, wherein $R_1$, $R_2$ and $R_3$, independently, are hydrogen, chloro or methyl, $R_{14}$ is $C_{1-2}$alkyl, $A_2$ is unsubstituted ethylene or phenylene and Q is —$NR_{18}'R_{19}'$, where $R_{18}'$ and $R_{19}'$, independently, are $C_{1-2}$alkyl.

* * * * *